US011882871B2

(12) United States Patent
Lu et al.

(10) Patent No.: US 11,882,871 B2
(45) Date of Patent: Jan. 30, 2024

(54) DETACHABLE ATOMIZING DEVICE AND CONTAINER THEREOF

(71) Applicant: MICROBASE TECHNOLOGY CORP., Taoyuan (TW)

(72) Inventors: Chih-Wei Lu, Taoyuan (TW); Chen-Hsiang Sang, Taoyuan (TW); Liang-Rern Kung, Taoyuan (TW); Wei-Zhe Cai, Taoyuan (TW); Jo-Ling Wu, Taoyuan (TW); Shu-Pin Hsieh, Taoyuan (TW)

(73) Assignee: MICROBASE TECHNOLOGY CORP., Taoyuan (TW)

( * ) Notice: Subject to any disclaimer, the term of this patent is extended or adjusted under 35 U.S.C. 154(b) by 388 days.

(21) Appl. No.: 16/981,755

(22) PCT Filed: Apr. 10, 2019

(86) PCT No.: PCT/CN2019/082094

§ 371 (c)(1),
(2) Date: Sep. 17, 2020

(87) PCT Pub. No.: WO2019/196876

PCT Pub. Date: Oct. 17, 2019

(65) Prior Publication Data

US 2021/0094059 A1 Apr. 1, 2021

Related U.S. Application Data

(60) Provisional application No. 62/656,343, filed on Apr. 11, 2018.

(51) Int. Cl.
*A24F 40/42* (2020.01)
*A61M 11/00* (2006.01)
(Continued)

(52) U.S. Cl.
CPC .............. *A24F 40/05* (2020.01); *A24F 40/42* (2020.01); *A61M 11/00* (2013.01); *B05B 17/0676* (2013.01); *A24F 40/10* (2020.01)

(58) Field of Classification Search
CPC . B05B 17/06; B05B 17/0638; B05B 17/0607; B05B 17/0646; B05B 17/0676;
(Continued)

(56) References Cited

U.S. PATENT DOCUMENTS 9,126,218 B2 * 9/2015 Sasaki ..................... B05B 17/06
9,339,838 B2 * 5/2016 Moran ............. A61M 15/0085
(Continued)

FOREIGN PATENT DOCUMENTS

CN 101843944 A 9/2010
CN 203842759 U 9/2014
(Continued)

OTHER PUBLICATIONS

WIPO, International Search Report dated May 24, 2019.

*Primary Examiner* — Christopher R Dandridge
(74) *Attorney, Agent, or Firm* — Li & Cai Intellectual Property (USA) Office

(57) ABSTRACT

A detachable atomizing device and a container thereof are provided. The container is detachably assembled to an atomizing assembly. The container includes a cup and a flexible film. The cup has an opening arranged at an end thereof, the flexible film covers the opening of the cup, and the flexible film has a tension region and an outer ring-shaped region that surrounds the tension region. The tension region has a plurality of atomizing holes having an average diameter within a range of 1 μm to 20 μm, and the outer ring-shaped region is attached to the cup. When the cup is assembled to the atomizing assembly, a tension value of the tension region of the flexible film is increased from an initial tension value to an atomizing tension value by being pressed from the atomizing assembly, and the atomizing holes of the tension region are configured to allow liquid to pass therethrough and to be formed as aerosol mist having an average atomized particle diameter less than a predetermined value. Accordingly, the cup and the flexible film that often need to be replaced are isolated from the atomizing assembly, and an expensive vibrator is disposed in the atomizing assembly, so that the service life of the detachable atomizing device can be extended.

20 Claims, 12 Drawing Sheets

(51) Int. Cl.

| | |
|---|---|
| ***B05B 17/06*** | (2006.01) |
| ***A24F 40/10*** | (2020.01) |
| ***A24F 40/05*** | (2020.01) |

(58) Field of Classification Search
CPC ....... A24F 40/05; A24F 40/42; A61M 11/001; A61M 11/005; A61M 15/0085; A61M 15/009
See application file for complete search history.

(56) References Cited

U.S. PATENT DOCUMENTS

| | | | |
|---|---|---|---|
| 9,452,441 | B2 | 9/2016 | Hsieh et al. |
| 10,420,903 | B2 | 9/2019 | Chen et al. |
| 2014/0110500 | A1 | 4/2014 | Crichton et al. |
| 2018/0021528 | A1 | 1/2018 | Hsieh et al. |
| 2019/0117908 | A1 | 4/2019 | Hsieh et al. |

FOREIGN PATENT DOCUMENTS

| | | | |
|---|---|---|---|
| CN | 204769366 | U | 11/2015 |
| CN | 105311718 | A | 2/2016 |
| CN | 205198620 | U | 5/2016 |
| CN | 107427649 | A | 12/2017 |
| CN | 107626020 | A | 1/2018 |
| WO | 2011083380 | A1 | 7/2011 |
| WO | 2011141475 | A1 | 11/2011 |
| WO | WO 2014097939 | A1 | 6/2014 |
| WO | WO 2016133856 | A2 | 8/2016 |
| WO | 2018017627 | A1 | 1/2018 |

* cited by examiner

DETACHABLE ATOMIZING DEVICE AND CONTAINER THEREOF

CROSS-REFERENCE TO RELATED PATENT APPLICATION

This application claims priority from the U.S. Provisional Patent Application Ser. No. 62/656,343 filed Apr. 11, 2018, which application is incorporated herein by reference in its entirety.

FIELD OF THE DISCLOSURE

The present disclosure relates to an atomizing device, and more particularly to a detachable atomizing device and a container thereof.

BACKGROUND OF THE DISCLOSURE

A conventional atomizing device is used to convert liquid into aerosol mist for user inhale. The conventional atomizing device needs to be thrown away the whole device when any one of components of the conventional atomizing device is damaged, so that some expensive components (e.g., a vibrator) will also be thrown even it still work. Accordingly, the conventional atomizing device needs to be developed in a way that the components can be replaced in order to extend the service life of an expensive one of the components.

However, in the process of developing the conventional atomizing device to have replaceable components, an important issue which needs to be overcome is: how to precisely match the replaceable components with the vibrator so that the atomizing device can be used to precisely atomize liquid.

SUMMARY OF THE DISCLOSURE

In response to the above-referenced technical inadequacies, the present disclosure provides a detachable atomizing device and a container thereof to effectively improve on the issues associated with conventional atomizing devices.

In one aspect, the present disclosure provides a detachable atomizing device, which includes an atomizing assembly and a container that is detachably assembled to the atomizing assembly. The atomizing assembly includes a bottom seat and a vibrator. The bottom seat has an assembling chamber, an aerosol chamber, and a communicating hole that is in spatial communication with the assembling chamber and the aerosol chamber. The assembling chamber, the aerosol chamber, and the communicating hole are formed in an interior of the bottom seat. The vibrator is disposed in the assembling chamber and has an abutting portion corresponding in position to the communicating hole. An inner edge of the abutting portion defines a thru-hole that is in spatial communication with the communicating hole. The container includes a cup and a flexible film. The cup has an opening arranged at an end thereof. The flexible film covers the opening and has a tension region and an outer ring-shaped region that surrounds the tension region. The tension region has a plurality of atomizing holes, and the outer ring-shaped region is attached to the cup. The cup is detachably disposed on the atomizing assembly, and the flexible film is arranged in the assembling chamber and is pressed by the abutting portion, so that the tension region is pressed to increase a tension value thereof from an initial tension value to an atomizing tension value, and the atomizing holes of the tension region are configured to allow liquid to pass therethrough and to be formed as aerosol mist having an average atomized particle diameter less than 5 μm.

In certain embodiments, the vibrator includes a carrier sheet and a vibration plate. The carrier sheet has a first surface and a second surface that is opposite to the first surface, and the carrier sheet has the abutting portion protruding from the first surface. The vibration plate is attached to the second surface of the carrier sheet, and the vibration plate is spaced apart from an inner surface of the assembling chamber.

In certain embodiments, the atomizing assembly includes a top seat assembled to the bottom seat, and a peripheral portion of the carrier sheet is clamped between the top seat and the bottom seat.

In certain embodiments, the bottom seat has a plurality of positioning pillars, the top seat has a plurality of fixing tubes, the peripheral portion of the carrier sheet is engaged with the positioning pillars, and the positioning pillars are respectively inserted into the fixing tubes, so that the fixing tubes press the peripheral portion of the carrier sheet.

In certain embodiments, the vibration plate includes two electrodes, and the detachable atomizing device further includes a cable connector. The cable connector has a cable end portion and a connector end portion. The cable end portion of the cable connector is clamped between the bottom seat and the top seat and is electrically coupled to the two electrodes of the vibration plate.

In certain embodiments, when the container is disposed in the top seat, the container is moved relative to the top seat by a movement distance, so that the flexible film is pressed by the abutting portion.

In certain embodiments, the cup has at least one positioning protrusion formed on an outer surface thereof, the top seat has at least one accommodating slot recessed in an inner surface thereof and at least one retaining slot that is recessed in the inner surface thereof and that is in spatial communication with the at least one accommodating slot, and the top seat has a bump formed in the at least one retaining slot. The at least one positioning protrusion of the cup is held in the at least one retaining slot by traveling through the at least one accommodating slot and traveling across the bump.

In certain embodiments, the vibrator includes a carrier sheet and a vibration plate. The carrier sheet has a first surface and a second surface that is opposite to the first surface, and the carrier sheet has the abutting portion protruding from the first surface. The vibration plate is in a ring-shape and is attached to the first surface of the carrier sheet, and the vibration plate surrounds an outer side of the abutting portion.

In certain embodiments, an inner diameter of the opening is greater than or equal to an outer diameter of the abutting portion, and at last part of the abutting portion is arranged in the opening.

In certain embodiments, an average diameter of the atomizing holes is within a range of 2.5 μm to 5 μm, the initial tension value of the tension region is 0, and the atomizing tension value of the tension region is within a range of 1.5 N/per unit area to 26.5 N/per unit area.

In certain embodiments, the flexible film is pressed along a height direction by the abutting portion, and the tension region is pressed along the height direction to have a displacement of an interference distance, so that the tension value of the tension region is increased from the initial tension value to the atomizing tension value.

In certain embodiments, the interference distance is greater than or equal to 100 μm.

In certain embodiments, the initial tension value of the tension region is 0, and the atomizing tension value of the tension region is greater than or equal to 1.5 N/per unit area.

In certain embodiments, the initial tension value of the tension region is 0, and the interference distance is within a range of 100 μm to 500 μm. When the interference distance is 100 μm, the atomizing tension value of the tension region is greater than or equal to 1.5 N/per unit area. When the interference distance is 500 μm, the atomizing tension value of the tension region is less than or equal to 26.5 N/per unit area.

In another aspect, the present disclosure provides a container of a detachable atomizing device for being detachably assembled to an atomizing assembly. The container includes a cup and a flexible film. The cup has an opening arranged at an end thereof. The flexible film covers the opening and has a tension region and an outer ring-shaped region that surrounds the tension region. The tension region has a plurality of atomizing holes having an average diameter within a range of 1 μm to 20 μm, and the outer ring-shaped region is attached to the cup. When the cup is assembled to the atomizing assembly, the outer ring-shaped region of the flexible film is pressed by the atomizing assembly, so that a tension value of the tension region is increased from an initial tension value to an atomizing tension value, and the atomizing holes of the tension region are configured to allow liquid to pass there-through and to be formed as aerosol mist having an average atomized particle diameter less than a predetermined value.

In certain embodiments, the predetermined value is 5 μm.

In certain embodiments, the average diameter of the atomizing holes is within a range of 2.5 μm to 5 μm, the initial tension value of the tension region is 0, and the atomizing tension value of the tension region is within a range of 1.5 N/per unit area to 26.5 N/per unit area.

In certain embodiments, when the cup is assembled to the atomizing assembly, the tension region of the flexible film is pressed along a height direction to have a displacement of an interference distance, so that the tension value of the tension region is increased from the initial tension value to the atomizing tension value.

In certain embodiments, the interference distance is greater than or equal to 100 μm, the initial tension value of the tension region is 0, and the atomizing tension value of the tension region is greater than or equal to 1.5 N/per unit area.

In certain embodiments, the interference distance is within a range of 100 μm to 500 μm, and the initial tension value of the tension region is 0. When the interference distance is 100 μm, the atomizing tension value of the tension region is greater than or equal to 1.5 N/per unit area. When the interference distance is 500 μm, the atomizing tension value of the tension region is less than or equal to 26.5 N/per unit area.

Therefore, for the detachable atomizing device and the container of the present disclosure, the cup and the flexible film that often need to be replaced are isolated from the atomizing assembly, and the expensive vibrator is disposed in the atomizing assembly, so that the service life of the detachable atomizing device can be extended. Specifically, since the structural cooperation between the container and the atomizing assembly (e.g., the flexible film is pressed by the abutting portion), the tension region can be pressed to increase the tension value thereof to the atomizing tension value so as to provide a precise atomizing effect. In other words, the atomizing holes of the tension region can be configured to allow liquid to pass there-through and to be formed as aerosol mist having the average atomized particle diameter less than the predetermined value (e.g., 5 μm).

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The present disclosure will become more fully understood from the following detailed description and accompanying drawings.

DETAILED DESCRIPTION OF THE EXEMPLARY EMBODIMENTS

Figure 1:
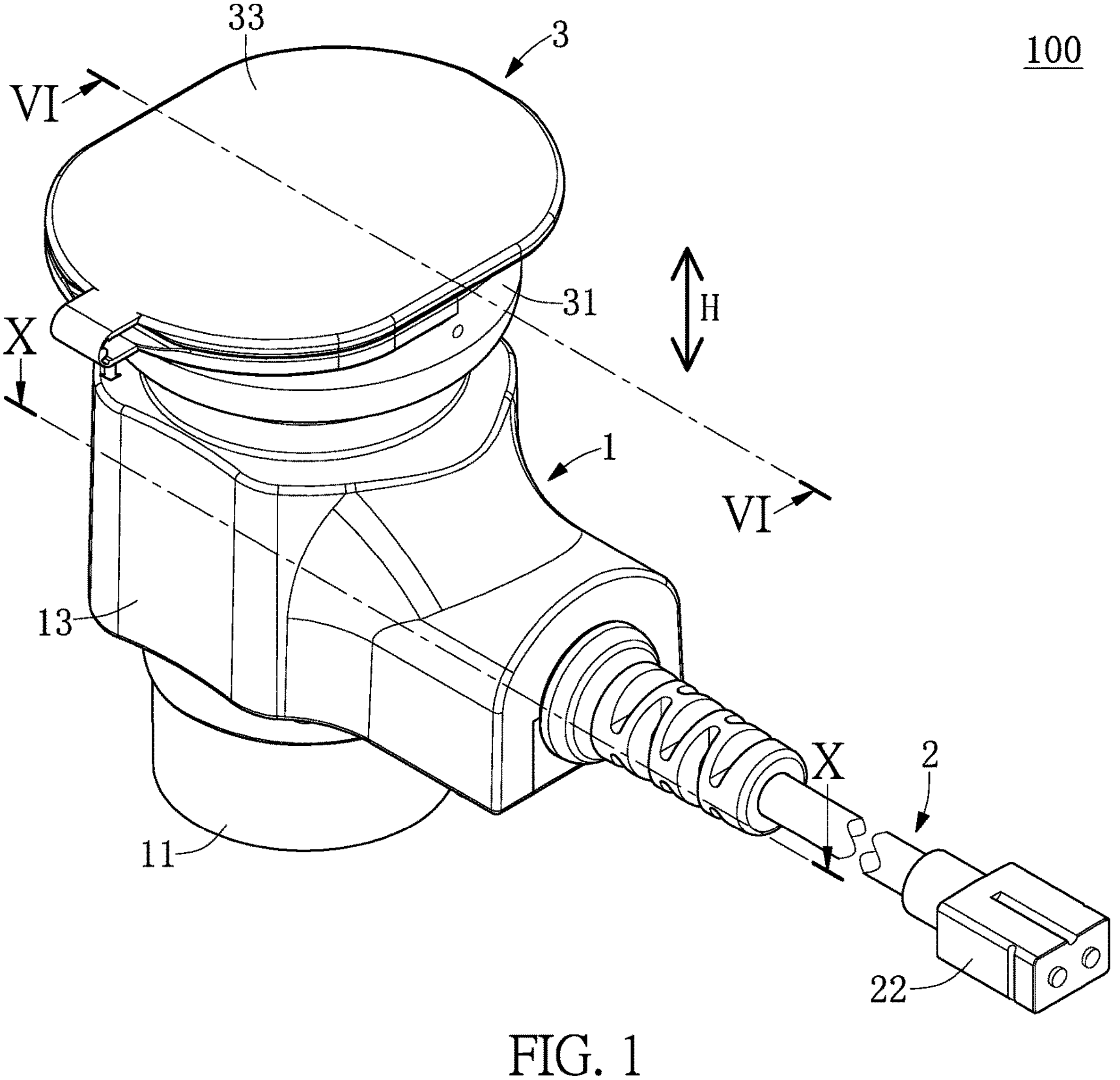
FIG. 1 is a perspective view of a detachable atomizing device according to a first embodiment of the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

First Embodiment

Figure 2:
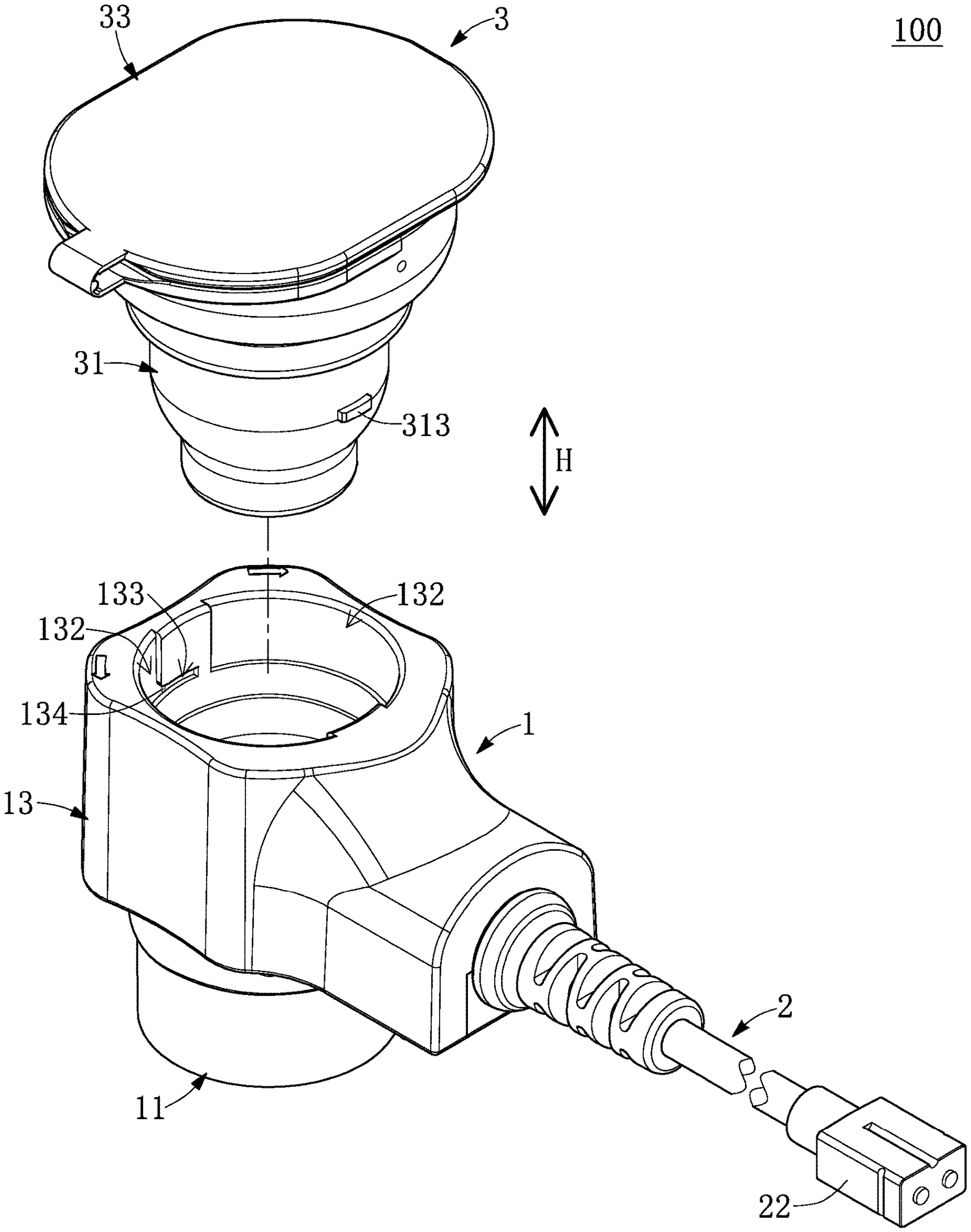
FIG. 2 is an exploded view of FIG. 1.
Figure 3:
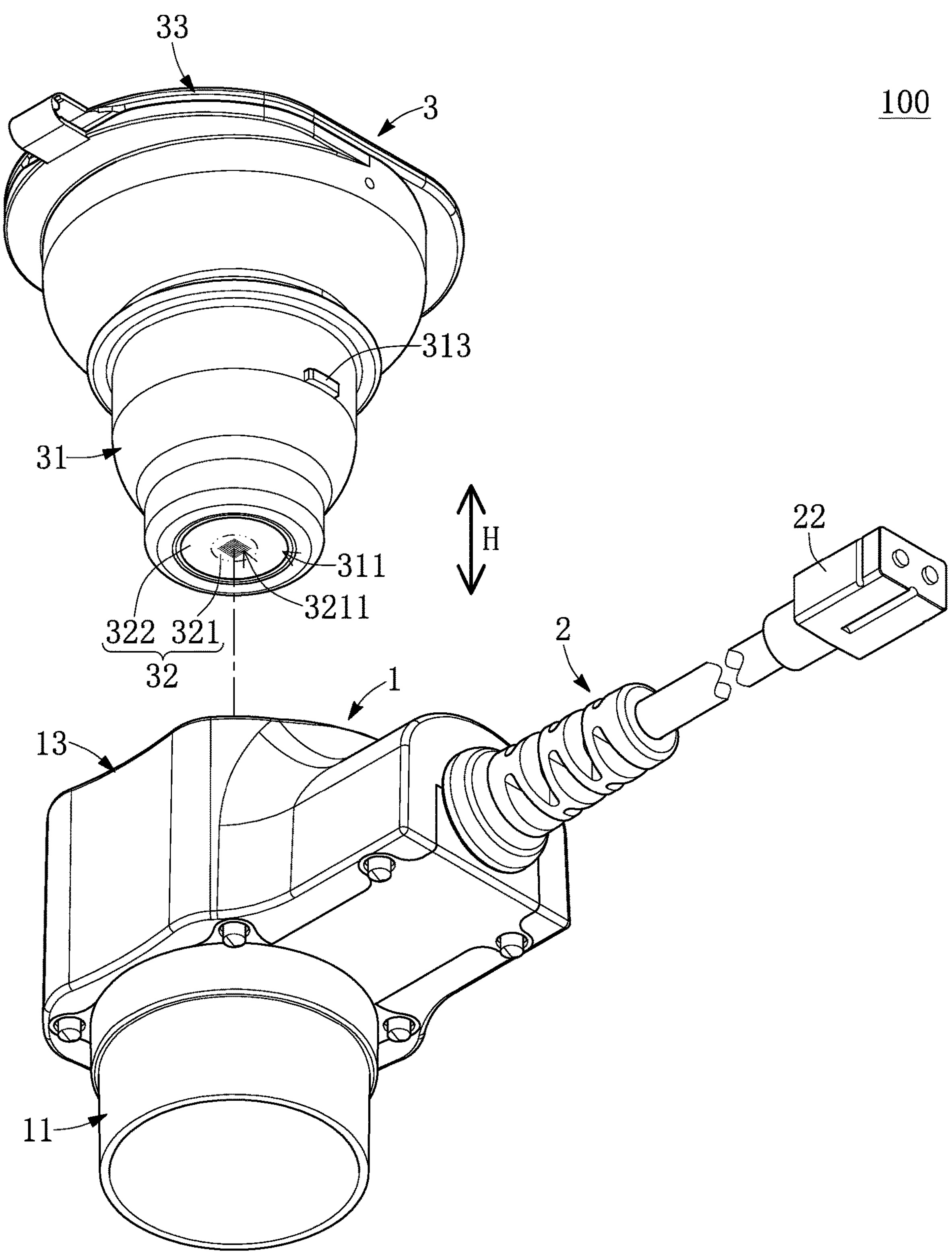
FIG. 3 is an exploded view of FIG. 1 from another angle of view.

Referring to FIG. 1 to FIG. 11, a first embodiment of the present disclosure provides a detachable atomizing device 100 that can be applicable to a medical field or a cosmetic field, but the present disclosure is not limited thereto. As shown in FIG. 1 to FIG. 3, the detachable atomizing device 100 includes an atomizing assembly 1, a cable connector 2 attached to the atomizing assembly 1, and a container 3 that is detachably assembled to the atomizing assembly 1. The atomizing assembly 1 and the container 3 are structurally connected to each other, but are not electrically coupled to each other. It should be noted that the container 3 in the present embodiment is described in cooperation with the atomizing assembly 1 and the cable connector 2, but the present disclosure is not limited thereto. For example, in other embodiments of the present disclosure, the container 3 can be independently used or can be used in cooperation with other components.

Figure 4:
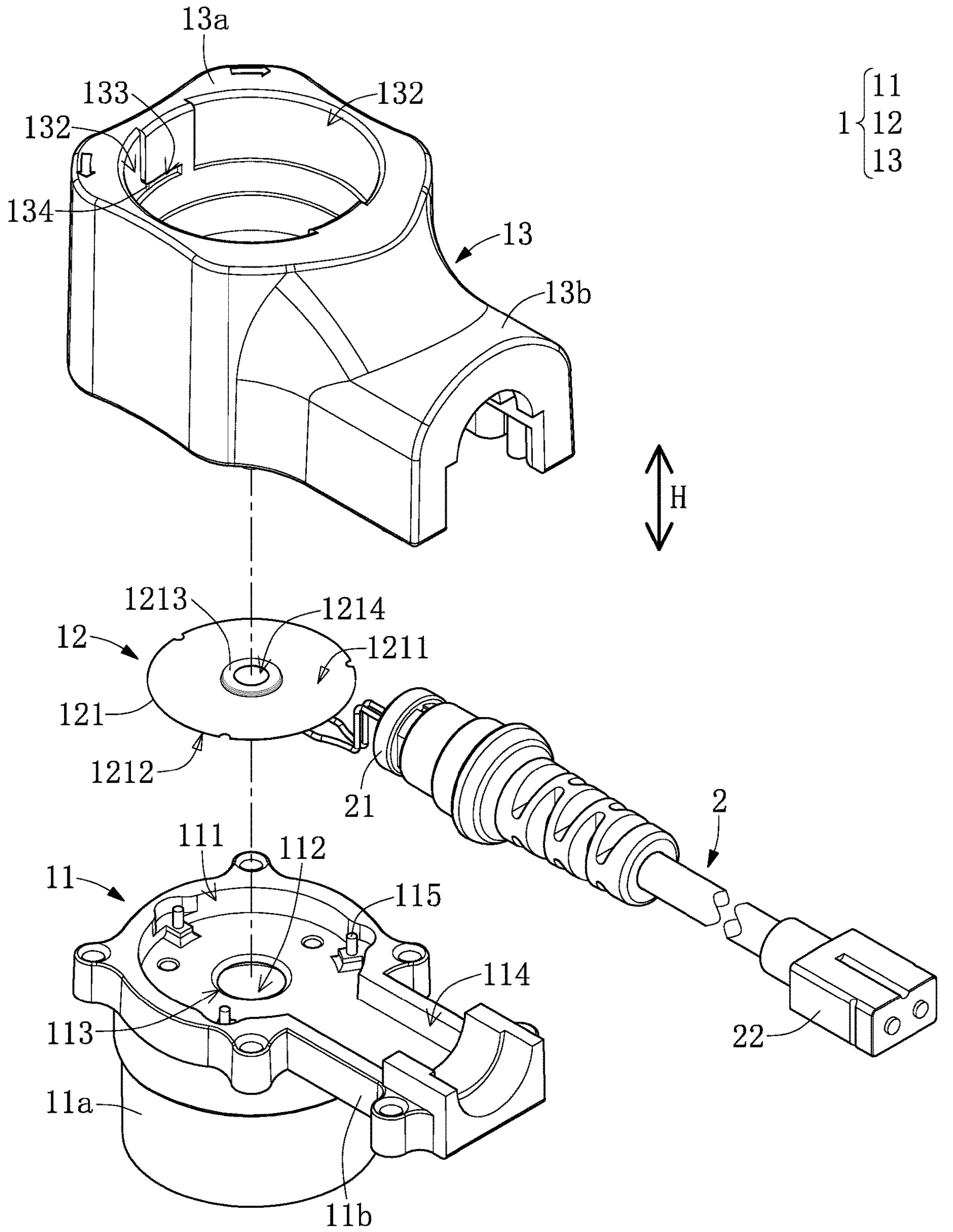
FIG. 4 is an exploded view of FIG. 2 with a container being omitted.
Figure 5:
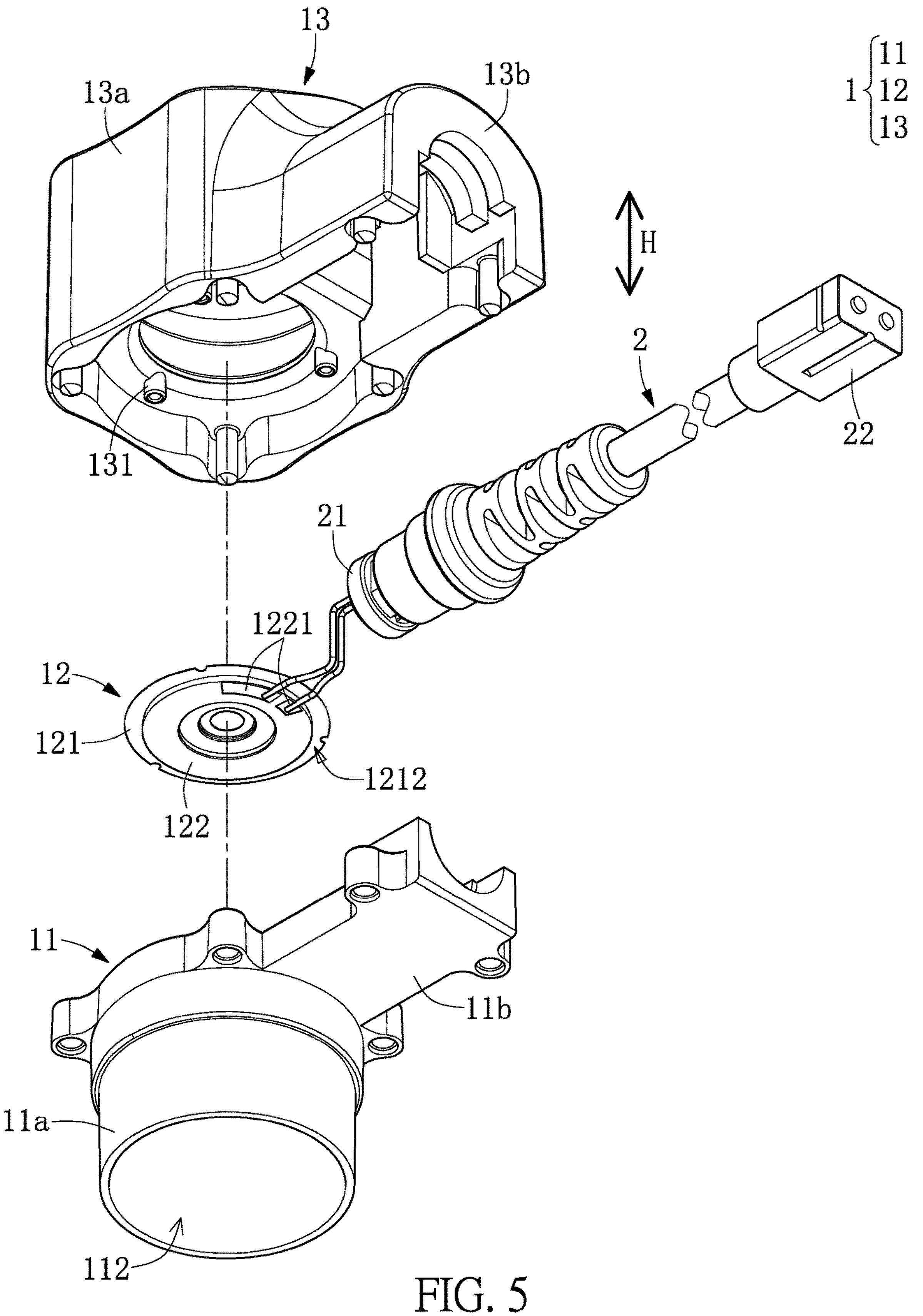
FIG. 5 is an exploded view of FIG. 3 with the container being omitted.
Figure 6:
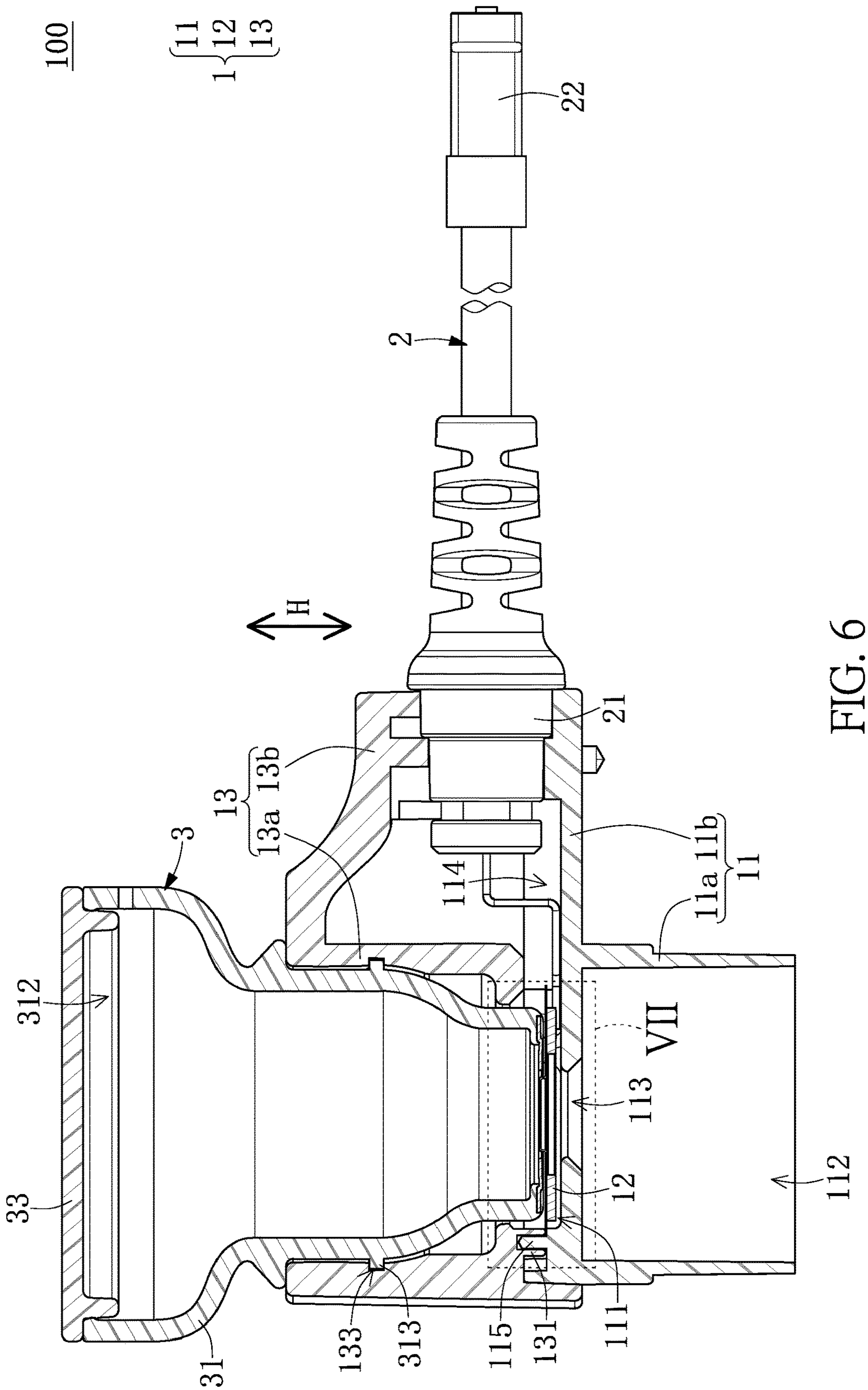
FIG. 6 is a cross-sectional view taken along line VI-VI of FIG. 1.

As shown in FIG. 4 to FIG. 6, the atomizing assembly 1 includes a bottom seat 11, a vibrator 12 disposed in the bottom seat 11, and a top seat 13 that is assembled to the bottom seat 11. An interior of the bottom seat 11 has an assembling chamber 111, an aerosol chamber 112, and a communicating hole 113 that is in spatial communication with the assembling chamber 111 and the aerosol chamber 112. Each of an inner diameter of the assembling chamber 111 and an inner diameter of the aerosol chamber 112 is greater than a diameter of the communicating hole 113. The assembling chamber 111 corresponds in position to the container 3, and the position of the aerosol chamber 112 is away from the container 3.

Specifically, the bottom seat 11 in the present embodiment includes a tubular structure 11*a* and a plate-like structure 11*b* that is integrally connected to the tubular structure 11*a*. An inner side of the tubular structure 11*a* forms the assembling chamber 111, the aerosol chamber 112, and the communicating hole 113. A portion of the tubular structure 11*a* corresponding in position to the assembling chamber 11 extends to form the plate-like structure 11*b*. The plate-like structure 11*b* has a cable groove 114 recessed therein, and the cable groove 114 is in spatial communication with the assembling chamber 111 of the tubular structure 11*a*.

As shown in FIG. 4 to FIG. 6, the vibrator 12 is disposed in the assembling chamber 111 of the bottom seat 11. The vibrator 12 in the present embodiment is in a ring-shape (e.g., a circular ring-shape) and includes a carrier sheet 121 and a vibration plate 122 that is in a ring-shape and that is attached to the carrier sheet 121. In other embodiments of the present disclosure, the shape of the vibration plate 122 can be adjusted according to design requirements (e.g., a circular shape or a rectangular shape). The vibrator 12 in the present embodiment is provided by two pieces of the carrier sheet 121 and the vibration plate 122, but the present disclosure is not limited thereto. For example, in other embodiments of the present disclosure, the vibrator 12 can be a one-piece structure.

As shown in FIG. 4 to FIG. 7, in the present embodiment, the carrier sheet 121 includes a first surface 1211 and a second surface 1212 that is opposite to the first surface 1211. The carrier sheet 121 has an abutting portion 1213 protruding from the first surface 1211, and the second surface 1212 of the carrier sheet 121 faces toward the communication hole 113 of the bottom seat 11. The abutting portion 1213 corresponds in position to the communication hole 113 of the bottom seat 11, and an inner edge of the abutting portion 1213 defines a thru-hole 1214 that is in spatial communication with the communicating hole 113. In other words, a projection region defined by orthogonally projecting an inner wall of the communication hole 113 onto the carrier sheet 121 along a height direction H is located at the abutting portion 1213 and surrounds an outer side of the thru-hole 1214.

Moreover, the vibration plate 122 is attached to the second surface 1212 of the carrier sheet 121, and the vibration plate 122 is spaced apart from an inner surface of the assembling chamber 111. An inner diameter of the vibration plate 122 is greater than an outer diameter of the abutting portion 1213, and an outer diameter of the vibration plate 122 is less than an outer diameter of the carrier sheet 121. A portion of the carrier sheet 121 attached to the vibration sheet 122 surrounds an outer side of the abutting portion 1213. Furthermore, the vibration plate 122 includes two electrodes 1221 arranged on a surface thereof (e.g., a bottom surface of the vibration plate 122 shown in FIG. 5) away from the carrier sheet 121, but the present disclosure is not limited thereto. For example, in other embodiments of the present disclosure, the two electrodes 1221 can be respectively arranged on two opposite surfaces of the vibration plate 122.

Specifically, in the present embodiment, a peripheral portion of the carrier sheet 12 is clamped between the bottom seat 11 and the top seat 13. The top seat 13 is detachably assembled to the bottom seat 11 along the height direction H. The top seat 13 includes a tubular housing 13*a* and a pressing housing 13*b* that is integrally connected to the tubular housing 13*a*. The tubular housing 13*a* of the top seat 13 is assembled to the tubular structure 11*a* of the bottom seat 11, and the tubular housing 13*a* and the tubular structure 11*a* are respectively formed with matching shapes for jointly clamping the vibrator 12. The following description describes the specific structures of the bottom seat 11 and the top seat 13 used for clamping the vibrator 12, but the present disclosure is not limited thereto.

In the present embodiment, the bottom seat 11 has a plurality of positioning pillars 115 (formed in a top portion of the tubular structure 11*a*), and the top seat 13 has a plurality of fixing tubes 131 (formed in a bottom portion of the tubular housing 13*a*). The peripheral portion of the carrier sheet 121 is engaged with the positioning pillars 115, and the positioning pillars 115 are respectively inserted into the fixing tubes 131, so that the fixing tubes 131 press the peripheral portion of the carrier sheet 121. However, the bottom seat 11 and the top seat 13 in the present disclosure are not limited to the above structures. For example, in other embodiments of the present disclosure, the positioning pillars 115 can be formed on the bottom seat 11, and the fixing tubes 113 can be formed on the top seat 13.

Moreover, the cable slot 114 formed in the plate-like structure 11*b* of the bottom seat 11 receives a part of the cable connector 2 (e.g., a cable end portion 21 disclosed in the following description), and the pressing housing 13*b* of the top seat 13 is assembled to the plate-like structure 11*b* of the bottom seat 11 for jointly clamping the part of the cable connector 2. The cable connector 2 includes a cable end portion 21 and a connector end portion 22. The cable end portion 21 is clamped between the bottom seat 11 and the top seat 13 and is electrically coupled to the two electrodes 1221 of the vibration plate 122, and the connector end portion 22 is configured to detachably connect to a power supply unit (not shown in the drawings).

In addition, the tubular housing 13*a* of the top seat 13 can be used to assemble with the container 3. Accordingly, when the container 3 is disposed in the top seat 13, the container 3 is moved relative to the top seat 13 by a movement distance so as to be interfered or pressed by the abutting portion 1213 (e.g., the flexible film 32 of the container 3 is pressed by the abutting portion 1213). The cooperation structure of the top seat 13 and the container 3 can be adjusted or changed according to design requirements, and is not limited by the drawings of the present embodiment. In the present embodiment, the top seat 13 has two accommodating slots 132 each being in a semi-circular ring-shape and recessed in an inner surface thereof (e.g., an inner surface of the tubular housing 13*a*) and two retaining slots 133 that are recessed in the inner surface thereof and that are respectively in spatial communication with the two accommodating slots 132 (e.g., each of the two retaining slots 133 is in spatial communication with only one of the two accommodating slots 132). The top seat 13 has two bumps 134 respectively formed in the two retaining slots 133. Each of the two retaining slots 133 is arranged between the two accommodating slots 132, and any one of the two bumps 134 is substantially located at an opening of the corresponding retaining slot 133. In other words, any one of the two accommodating slots 132 and the corresponding retaining slot 133 are 2-fold rotationally symmetrical to the other one of the two accommodating slots 132 and the corresponding retaining slot 133 with respect to a central axis of the tubular housing 13*a*.

Figure 8:
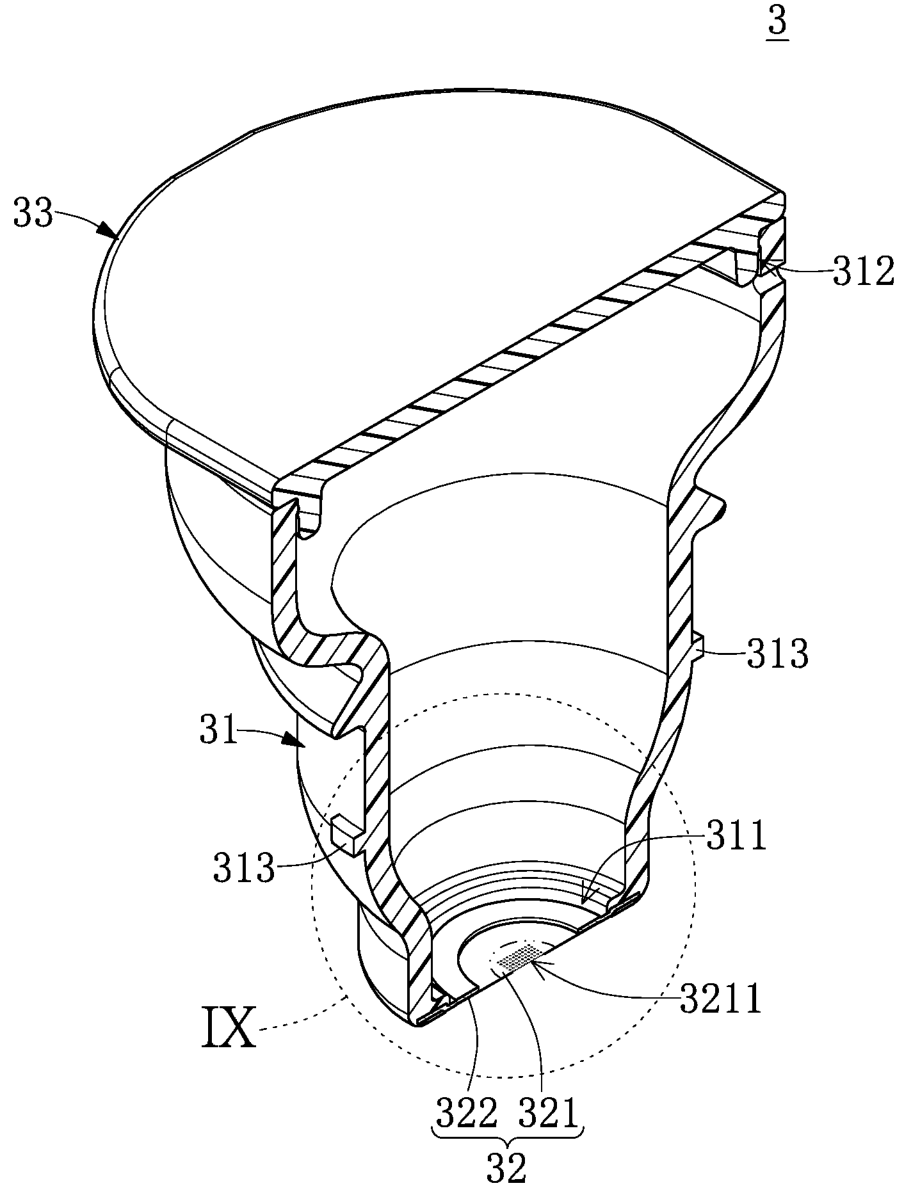
FIG. 8 is a perspective and cross-sectional view of the container according to the first embodiment of the present disclosure.
Figure 9:
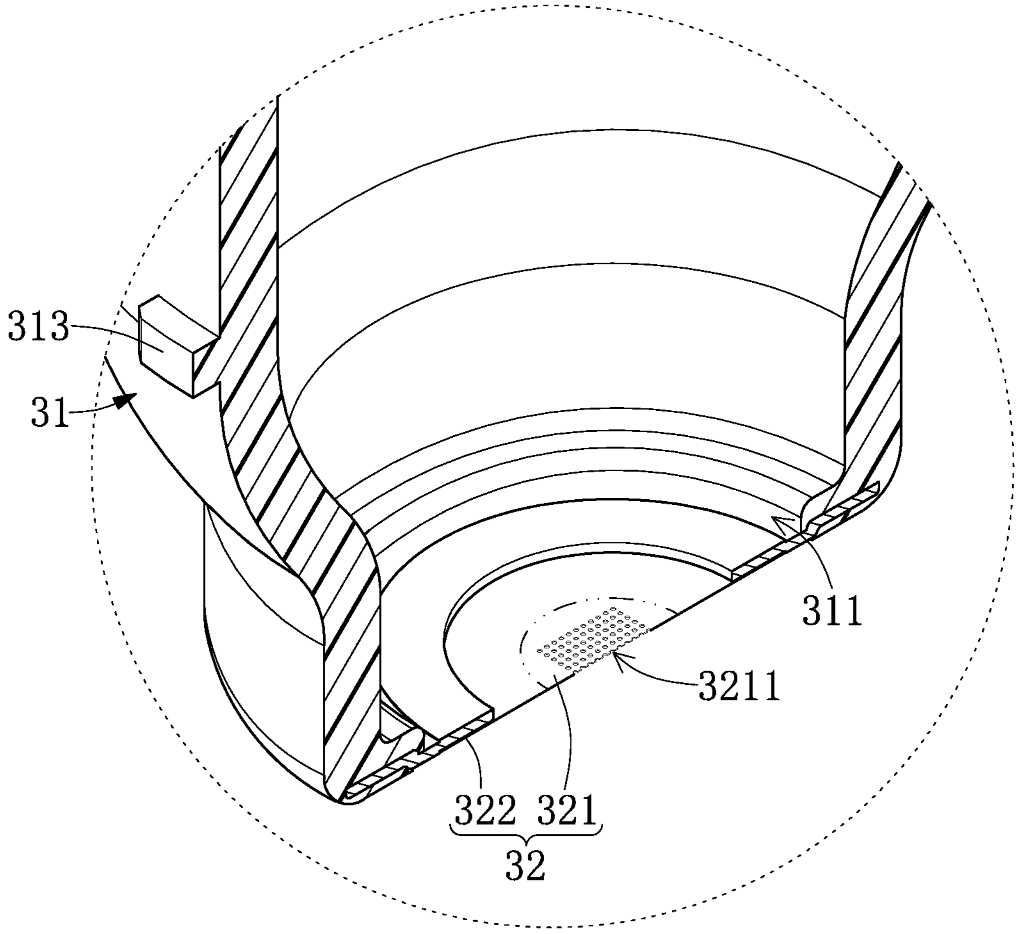
FIG. 9 is an enlarged view of part IX of FIG. 8.

As shown in FIG. 8 and FIG. 9, the container 3 includes a cup 31, a flexible film 32 attached to the cup 31, and a lid 33 that detachably covers the cup 31. An end of the cup 31 has an opening 311, and another end of the cup 31 has a liquid inlet 312. In the present embodiment, an inner diameter of the liquid inlet 312 is greater than an inner diameter of the opening 311, and the inner diameter of the opening 311 is greater than or equal to the outer diameter of the abutting portion 1213 of the carrier sheet 121. The lid 33 is bendably connected to a portion of the cup 31 adjacent to the liquid inlet 312, so that the lid 33 can be engaged with the cup 31 to cover the liquid inlet 312.

Figure 10:
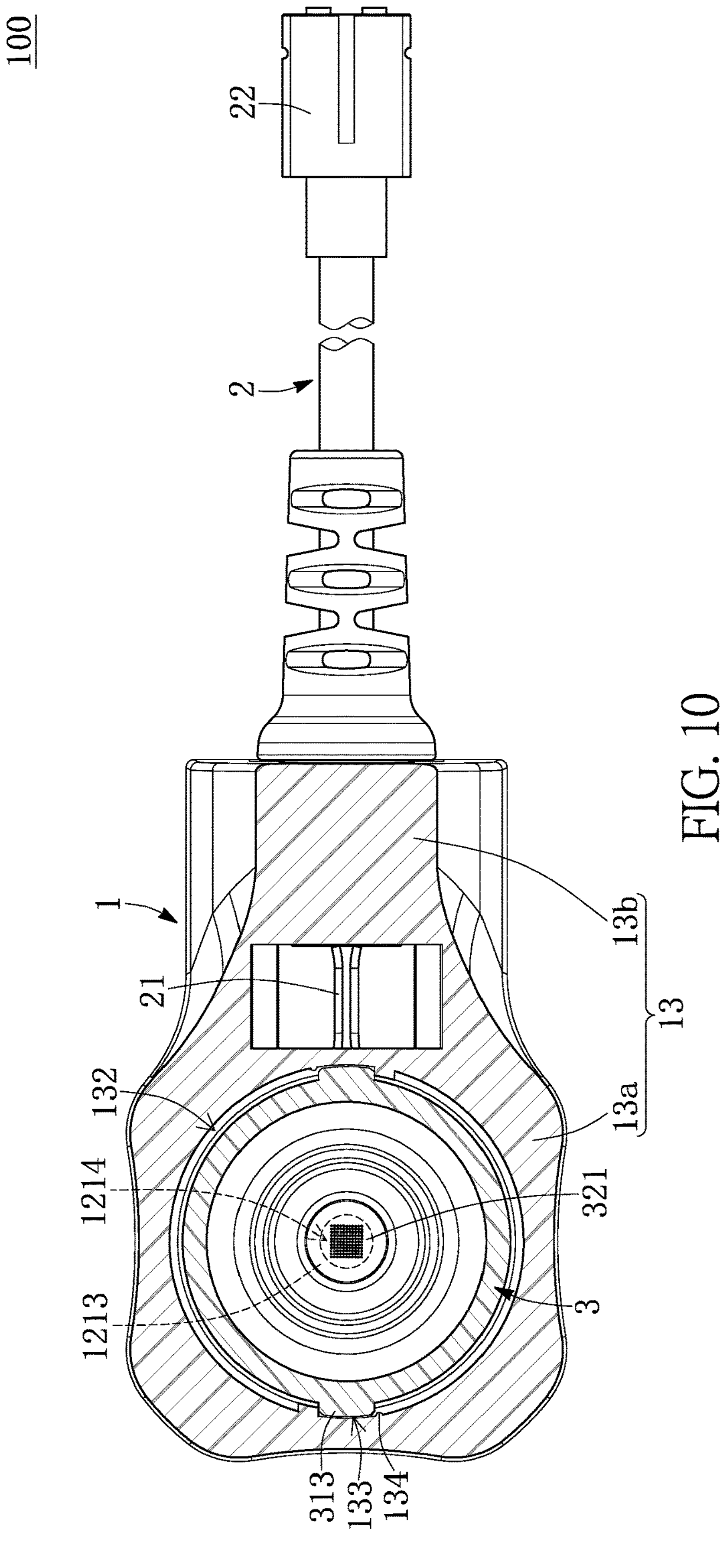
FIG. 10 is a cross-sectional view taken along line X-X of FIG. 1.

Moreover, as shown in FIG. 2 and FIG. 10, the cup 31 has two positioning protrusions 313 formed on two opposite sides of an outer surface thereof. When the cup 31 is assembled to the top seat 13, the two positioning protrusions 313 of the cup 31 are respectively held in the two retaining slots 133 by respectively traveling through the two accommodating slots 132 and respectively traveling across the two bumps 134. Each of the two retaining slots 133 and the corresponding bump 134 are configured to hold one of the two positioning protrusions 313 there-between, thereby maintaining the relative position of the cup 31 and the top seat 13. In addition, the quantity of any one of the positioning protrusions 313, the accommodating slots 132, and the retaining slots 133 can be at least one, and the shape of any one of the accommodating slots 132 is not limited to the semi-circular ring-shape.

As shown in FIG. 8 and FIG. 9, the flexible film 32 includes a tension region 321 and an outer ring-shaped region 322 that surrounds the tension region 321. The outer ring-shaped region 322 is attached to the cup 31, so that the flexible film 32 covers the opening 311. The tension region 321 in the present embodiment is in a circular shape and has a radius of substantial 1.5 mm. Moreover, the tension region 321 has a plurality of atomizing holes 3211 having an average diameter that can be within a range of 1 μm to 10 μm (e.g., the average diameter is preferably within a range of 2.5 μm to 5 μm), but the present disclosure is not limited thereto. For example, the tension region 321 of the flexible film 32 can have a plurality of atomizing holes 3211 having an average diameter within a range of 1 μm to 20 μm. In addition, the shape and arrangement of the atomizing holes 3211 can be adjusted according to design requirements (e.g., the atomizing holes 3211 are in an irregular arrangement or are distributed on an entirety of the tension region 321). The atomizing holes 3211 of the flexible film 32 in the present embodiment are formed in the tension region 321, but it does not exclude that the atomizing holes 3211 are further formed in the outer ring-shaped region 322 arranged outside of the tension region 321.

Figure 7:
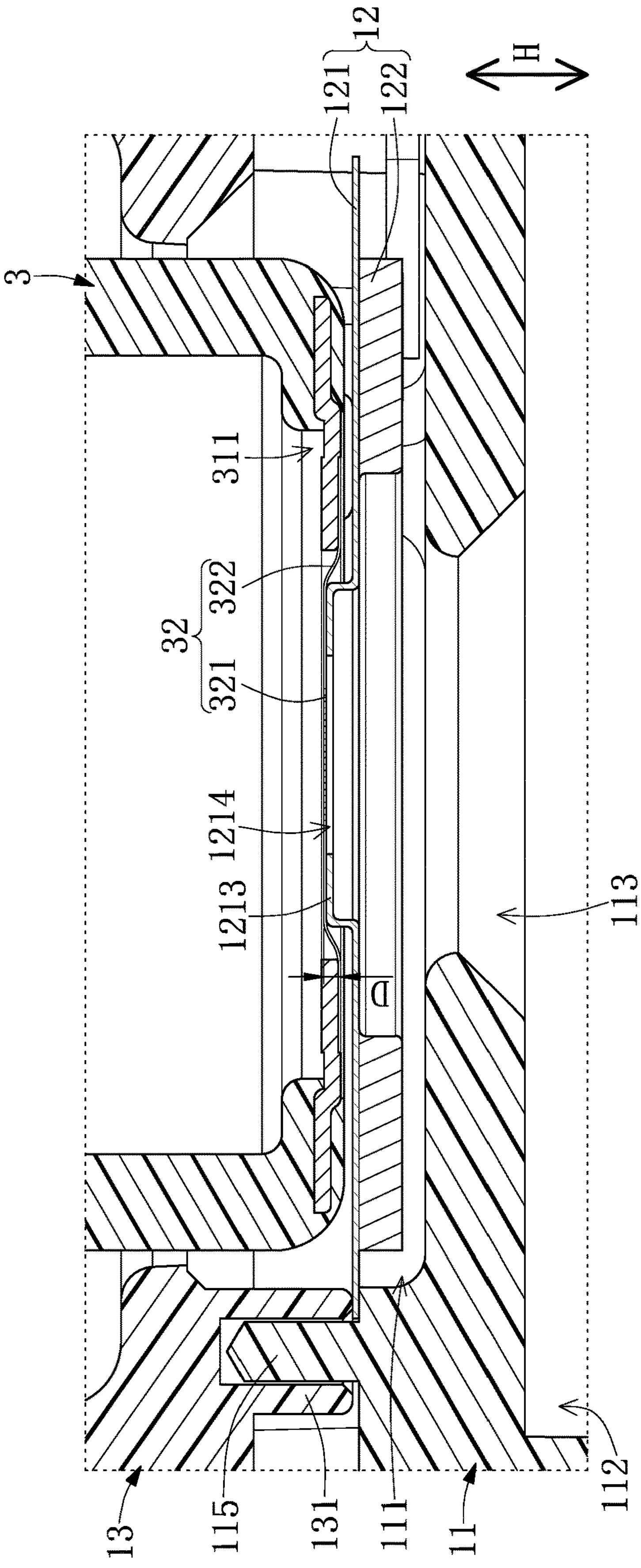
FIG. 7 is an enlarged view of part VII of FIG. 6.

Before the container 3 is assembled to the atomizing assembly 1, the tension region 321 of the flexible film 32 in the present embodiment has an initial tension value that is 0, but the present disclosure is not limited thereto. For example, in other embodiments of the present disclosure, the initial tension value of the tension region 321 can be greater than 0 Moreover, as shown in FIG. 6 and FIG. 7, when the container 3 is assembled to the atomizing assembly 1, the outer ring-shaped region 322 of the flexible film 32 is pressed by the atomizing assembly 1, so that a tension value of the tension region 321 is increased from the initial tension value to an atomizing tension value, and the atomizing holes 3211 of the tension region 321 are configured to allow liquid to pass there-through and to be formed as aerosol mist having an average atomized particle diameter less than a predetermined value.

The atomizing tension value of the tension region 321 is within a range of 1.5 N/per unit area to 26.5 N/per unit area. In the present embodiment, per unit area is an area of the tension region 321 (e.g., 2.25 π $mm^2$), and the predetermined value is 5 μm, but the present disclosure is not limited thereto.

Specifically, when the container 3 is assembled to the atomizing assembly 1, the abutting portion 1213 is at least partially arranged in the opening 311 of the container 3, and the flexible film 32 of the container 3 is arranged in the assembling chamber 111 and is pressed by the abutting portion 1213, so that the tension region 321 is pressed to increase the tension value thereof from the initial tension value to the atomizing tension value, and the atomizing holes 3211 of the tension region 321 are configured to allow liquid to pass there-through and to be formed as aerosol mist having the average atomized particle diameter less than 5 μm.

The flexible film 32 in the present embodiment is pressed along the height direction H by the abutting portion 1213, and the tension region 321 is pressed along the height direction H to have a displacement of an interference distance D, so that the tension value of the tension region 321 is increased from the initial tension value to the atomizing tension value. In other words, the tension value of the tension region 321 in the present embodiment can be adjusted by changing the interference distance D, but the present disclosure is not limited thereto.

In the present embodiment, the interference distance D is controlled to be greater than or equal to 100 μm, and the atomizing tension value of the tension region 321 is greater than or equal to 1.5 N/per unit area, so that the predetermined value can be maintained at 5 μm.

Figure 11:
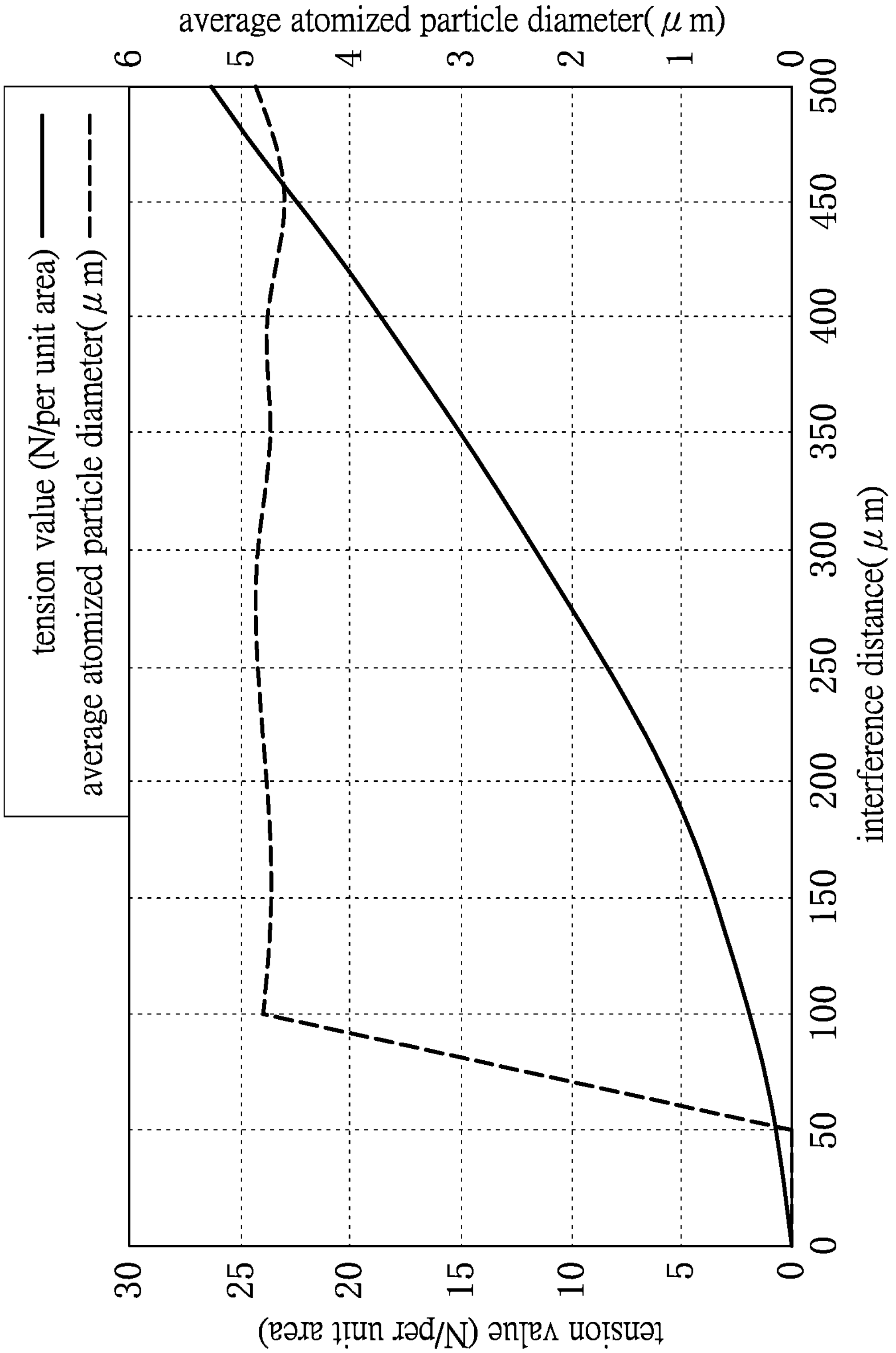
FIG. 11 is a testing diagram of the detachable atomizing device according to a first embodiment of the present disclosure.

Specifically, according to a testing result shown in FIG. 11, the interference distance D is preferably within a range of 100 μm to 500 μm; when the interference distance D is 100 μm, the atomizing tension value of the tension region 321 is greater than or equal to 1.5 N/per unit area; and when the interference distance D is 500 μm, the atomizing tension value of the tension region 321 is less than or equal to 26.5 N/per unit area.

In addition, the interference distance D in the present embodiment is formed by moving the container 3 so as to cause the flexible film 32 to be pressed by the abutting portion 1213 of the atomizing assembly 1, but the combination manner between the atomizing assembly 1 and the container 3 can be adjusted or changed according to design requirements and is not limited to the present embodiment. For example, in other embodiments of the present disclosure, when the container 3 is assembled to the atomizing assembly 1, the atomizing assembly 1 can be manipulated to move the abutting portion 1213 to press the tension region 321 of the flexible film 32, thereby achieving the displacement of the tension region 321 to be the interference distance D.

Second Embodiment

Figure 12:
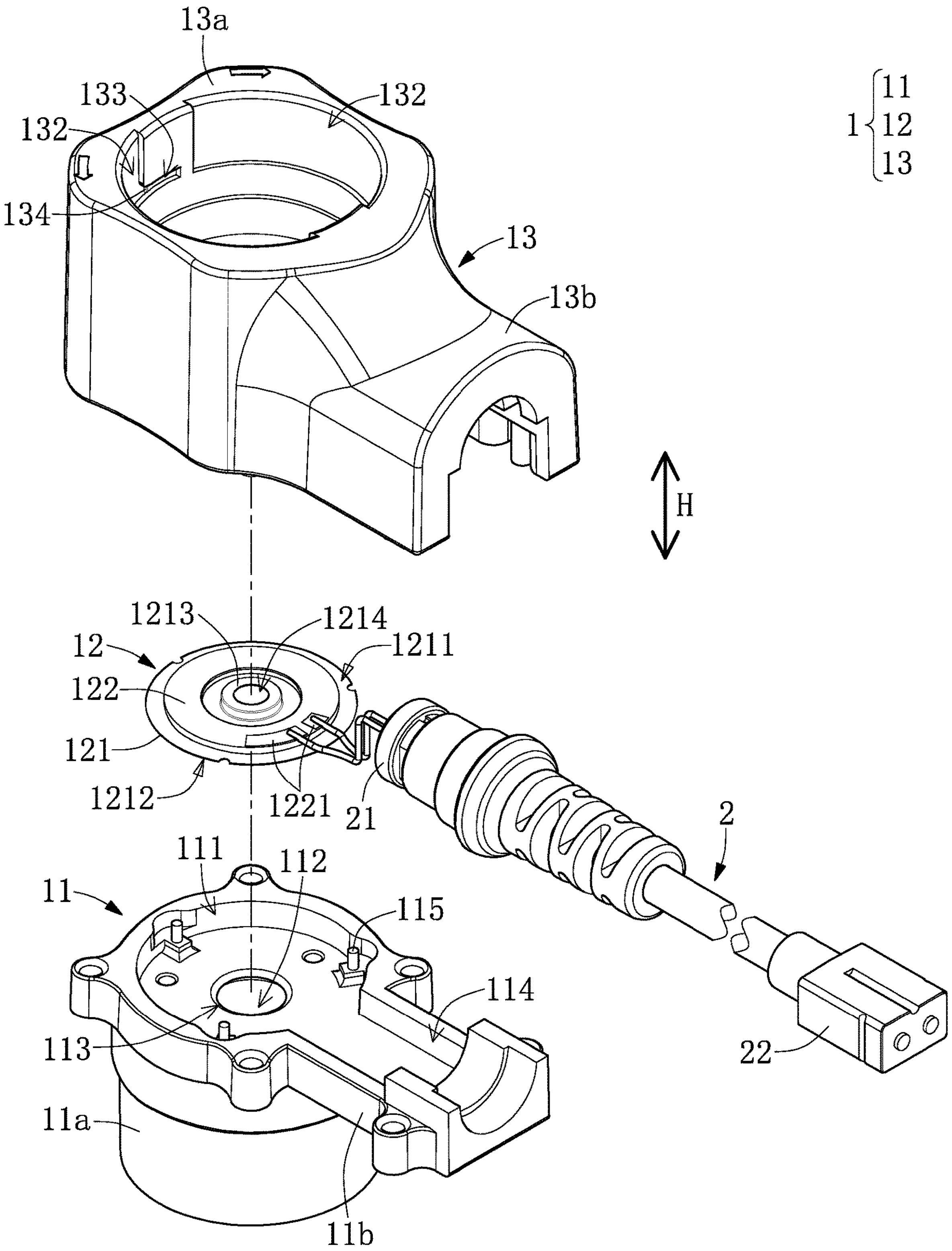
FIG. 12 is a perspective view of a detachable atomizing device according to a second embodiment of the present disclosure.

Referring to FIG. 12, a second embodiment of the present disclosure is similar to the first embodiment of the present disclosure. For the sake of brevity, descriptions of the same components in the first and second embodiments of the present disclosure (e.g., the bottom seat 11 and the top seat 13 of the atomizing assembly 1, the container 3, and the cable connector 2) will be omitted herein, and the different features between the first and second embodiments mainly reside in the vibrator 12.

Specifically, the vibration plate 122 in the present embodiment is attached to the first surface 1211 of the carrier sheet 121, the vibration plate 122 surrounds an outer side of the abutting portion 1213, and the second surface 1212 of the carrier sheet 121 faces toward the communication hole 113 of the bottom seat 11. In other words, under the same interference distance D, a distance between the abutting portion 1213 and the first surface 1211 of the carrier sheet 121 of the present embodiment is greater than a distance between the abutting portion 1213 and the first surface 1211 of the carrier sheet 121 of the first embodiment.

In conclusion, for the detachable atomizing device and the container of the present disclosure, the cup and the flexible film that often need to be replaced are isolated from the atomizing assembly, and the expensive vibrator is disposed in the atomizing assembly, so that the life cycle of the detachable atomizing device can be extended. Specifically, since the structural cooperation between the container and the atomizing assembly (e.g., the flexible film is pressed by the abutting portion), the tension region can be pressed to increase the tension value thereof to the atomizing tension value so as to provide a precise atomizing effect. In other words, the atomizing holes of the tension region can be configured to allow liquid to pass there-through and to be formed as aerosol mist having the average atomized particle diameter less than the predetermined value (e.g., 5 μm).

Moreover, for the detachable atomizing device disclosed of the present disclosure, the atomizing tension value of the tension region can be stably controlled by the structural cooperation between the container and the atomizing assembly (e.g., the positioning protrusion of the cup can be held in the retaining slot by traveling through the accommodating slot and traveling across the bump). The vibrator can be firmly disposed by being in structural cooperation with the bottom seat and the top seat (e.g., the peripheral portion of the carrier sheet is clamped between the top seat and the bottom seat).

In addition, for the detachable atomizing device disclosed of the present disclosure, the atomizing tension value of the flexible film of the container can be further controlled by the interference distance in the height direction (e.g., when the interference distance is 100 μm, the atomizing tension value of the tension region is greater than or equal to 1.5 N/per unit area; and when the interference distance is 500 μm, the atomizing tension value of the tension region is less than or equal to 26.5 N/per unit area).

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A detachable atomizing device, comprising:

an atomizing assembly including:

a bottom seat having an assembling chamber, an aerosol chamber, and a communicating hole that is in spatial communication with the assembling chamber and the aerosol chamber, wherein the assembling chamber, the aerosol chamber, and the communicating hole are formed in an interior of the bottom seat; and a vibrator disposed in the assembling chamber and having an abutting portion corresponding in position to the communicating hole, wherein an inner edge of the abutting portion defines a thru-hole that is in spatial communication with the communicating hole; and a container detachably assembled to the atomizing assembly and including:

a cup having an opening arranged at an end thereof; and a flexible film covering the opening and having a tension region and an outer ring-shaped region that surrounds the tension region, wherein the tension region has a plurality of atomizing holes, and the outer ring-shaped region is attached to the cup, wherein the cup is detachably disposed on the atomizing assembly, and the flexible film is arranged in the assembling chamber and is pressed by the abutting portion, so that the tension region is pressed to increase a tension value thereof from an initial tension value to an atomizing tension value, and the atomizing holes of the tension region are configured to allow liquid to pass there-through and to be formed as aerosol mist having an average atomized particle diameter less than 5 μm.

2. The detachable atomizing device according to claim 1, wherein the vibrator includes:

a carrier sheet having a first surface and a second surface that is opposite to the first surface, wherein the carrier sheet has the abutting portion protruding from the first surface; and a vibration plate attached to the second surface of the carrier sheet, wherein the vibration plate is spaced apart from an inner surface of the assembling chamber.

3. The detachable atomizing device according to claim 2, wherein the atomizing assembly includes a top seat assembled to the bottom seat, and a peripheral portion of the carrier sheet is clamped between the top seat and the bottom seat.

4. The detachable atomizing device according to claim 3, wherein the bottom seat has a plurality of positioning pillars, the top seat has a plurality of fixing tubes, the peripheral portion of the carrier sheet is engaged with the positioning pillars, and the positioning pillars are respectively inserted into the fixing tubes, so that the fixing tubes press the peripheral portion of the carrier sheet.

5. The detachable atomizing device according to claim 3, wherein the vibration plate includes two electrodes, and the detachable atomizing device further includes a cable connector, wherein the cable connector has a cable end portion and a connector end portion, and wherein the cable end portion of the cable connector is clamped between the bottom seat and the top seat and is electrically coupled to the two electrodes of the vibration plate.

6. The detachable atomizing device according to claim 3, wherein when the container is disposed in the top seat, the container is moved relative to the top seat by a movement distance, so that the flexible film is pressed by the abutting portion.

7. The detachable atomizing device according to claim 3, wherein the cup has at least one positioning protrusion formed on an outer surface thereof, the top seat has at least one accommodating slot recessed in an inner surface thereof and at least one retaining slot that is recessed in the inner surface thereof and that is in spatial communication with the at least one accommodating slot, and the top seat has a bump formed in the at least one retaining slot, and wherein the at least one positioning protrusion of the cup is held in the at least one retaining slot by traveling through the at least one accommodating slot and traveling across the bump.

8. The detachable atomizing device according to claim 1, wherein the vibrator includes:

a carrier sheet having a first surface and a second surface that is opposite to the first surface, wherein the carrier sheet has the abutting portion protruding from the first surface; and a vibration plate being in a ring-shape and attached to the first surface of the carrier sheet, wherein the vibration plate surrounds an outer side of the abutting portion.

9. The detachable atomizing device according to claim 1, wherein an inner diameter of the opening is greater than or equal to an outer diameter of the abutting portion, and at last part of the abutting portion is arranged in the opening.

10. The detachable atomizing device according to claim 1, wherein an average diameter of the atomizing holes is within a range of 2.5 μm to 5 μm, the initial tension value of the tension region is 0, and the atomizing tension value of the tension region is within a range of 1.5 N/per unit area to 26.5 N/per unit area.

11. The detachable atomizing device according to claim 1, wherein the flexible film is pressed along a height direction by the abutting portion, and the tension region is pressed along the height direction to have a displacement of an interference distance, so that the tension value of the tension region is increased from the initial tension value to the atomizing tension value.

12. The detachable atomizing device according to claim 11, wherein the interference distance is greater than or equal to 100 μm.

13. The detachable atomizing device according to claim 12, wherein the initial tension value of the tension region is 0, and the atomizing tension value of the tension region is greater than or equal to 1.5 N/per unit area.

14. The detachable atomizing device according to claim 11, wherein the initial tension value of the tension region is 0, and the interference distance is within a range of 100 μm to 500 μm, wherein when the interference distance is 100 μm, the atomizing tension value of the tension region is greater than or equal to 1.5 N/per unit area, and wherein when the interference distance is 500 μm, the atomizing tension value of the tension region is less than or equal to 26.5 N/per unit area.

15. A container of a detachable atomizing device capable of being detachably assembled to an atomizing assembly, the container comprising:

a cup having an opening arranged at an end thereof and at least one positioning protrusion formed on an outer surface thereof; and a flexible film having a tension region and an outer ring-shaped region that surrounds the tension region, wherein the tension region has a plurality of atomizing holes having an average diameter within a range of 1 μm to 20 μm, and the outer ring-shaped region is connected to the cup so as to enable the flexible film to seal the opening and prevent passage of a liquid therethrough when the container is detached from the atomizing assembly, wherein when the cup is assembled to the atomizing assembly by being rotated, the at least one positioning protrusion of the cup is held in at least one retaining slot of the atomizing assembly, the outer ring-shaped region of the flexible film is pressed by the atomizing assembly, so that a tension value of the tension region is increased from an initial tension value to an atomizing tension value, and the atomizing holes of the tension region are configured to allow the liquid to pass therethrough and to be formed as aerosol mist having an average atomized particle diameter less than a predetermined value.

16. The container according to claim 15, wherein the predetermined value is 5 μm.

17. The container according to claim 15, wherein the average diameter of the atomizing holes is within a range of 2.5 μm to 5 μm, the initial tension value of the tension region is 0, and the atomizing tension value of the tension region is within a range of 1.5 N/per unit area to 26.5 N/per unit area.

18. The container according to claim 15, wherein when the cup is assembled to the atomizing assembly, the tension region of the flexible film is pressed along a height direction to have a displacement of an interference distance, so that the tension value of the tension region is increased from the initial tension value to the atomizing tension value.

19. The container according to claim 18, wherein the interference distance is greater than or equal to 100 μm, the initial tension value of the tension region is 0, and the atomizing tension value of the tension region is greater than or equal to 1.5 N/per unit area.

20. The container according to claim 18, wherein the interference distance is within a range of 100 μm to 500 μm, and the initial tension value of the tension region is 0, wherein when the interference distance is 100 μm, the atomizing tension value of the tension region is greater than or equal to 1.5 N/per unit area, and wherein when the interference distance is 500 μm, the atomizing tension value of the tension region is less than or equal to 26.5 N/per unit area.

* * * * *